US00PP22535P2

(12) United States Plant Patent
Stemkens

(10) Patent No.: US PP22,535 P2
(45) Date of Patent: Feb. 28, 2012

(54) ***VERBENA* PLANT NAMED 'PUWYDENA'**

(50) Latin Name: *Verbena×hybrida*
Varietal Denomination: Puwydena

(75) Inventor: Henricus Godefriedus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/924,086

(22) Filed: Sep. 20, 2010

(51) Int. Cl.
*A01H 5/00* (2006.01)

(52) U.S. Cl. ..... Plt./308

(58) Field of Classification Search ..... Plt./308
See application file for complete search history.

*Primary Examiner* — Susan McCormick Ewoldt
(74) *Attorney, Agent, or Firm* — S. Matthew Edwards

(57) ABSTRACT

A new *Verbena* plant named 'Puwydena' particularly distinguished by the bold-medium violet colored flowers with a distinct white eye, medium green foliage, medium sized creeping and trailing plant habit with good branching and is early to flower.

1 Drawing Sheet

Latin name of the genus and species of the plant claimed: *Verbena×hybrida.*

Varietal denomination: 'Puwydena'.

BACKGROUND OF THE NEW PLANT

The present invention comprises a new *Verbena*, botanically known as *Verbena×hybrida*, and hereinafter referred to by the variety name 'Puwydena'.

'Puwydena' is a product of a planned breeding program. The new cultivar has bold-medium violet colored flowers with a distinct white eye, medium green foliage, medium sized creeping and trailing plant habit with good branching and is early to flower.

'Puwydena' originated from a open pollinated hybridization made in summer of 2005 in a controlled breeding environment in Enkhuizen, Netherlands. The female parent was the unpatented, proprietary plant designated 'G1031-1', with smaller purple flowers with a lighter edge and lighter leaves.

The male parent of 'Puwydena' was an unpatented, proprietary plant designated as 'G0997-3' with pink flowers, is later to flower and has 'entire' shaped margins on the foliage. The resultant seed was sown in February 2006.

'Puwydena' was selected as one flowering plant within the progeny of the stated cross in the August 2006 in a controlled environment in Enkhuizen, Netherlands.

The first act of asexual reproduction of 'Puwydena' was accomplished when vegetative cuttings were propagated from the initial selection in August 2006 in a controlled environment in Enkhuizen, Netherlands.

BRIEF SUMMARY OF INVENTION

Horticultural examination of plants grown from cuttings of the plant initiated in August 2006, and continuing thereafter, has demonstrated that the combination of characteristics as herein disclosed for 'Puwydena' are firmly fixed and are retained through successive generations of asexual reproduction.

'Puwydena' has not been observed under all possible environmental conditions. The phenotype may vary significantly with variations in environment such as temperature, light intensity and day length.

Plant Breeder's Right for this cultivar were applied for in Canada on Feb. 9, 2010 (10-6833) and in CPVO on Sep. 23, 2009 (2009/1859). 'Puwydena' has not been made publicly available more than one year prior to the filing of this application.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawing shows typical flower and foliage characteristics of 'Puwydena' with colors being as true as possible with an illustration of this type.

The photographic drawing shows a flowering potted plant of the new variety and a close-up of the flowers.

DETAILED BOTANICAL DESCRIPTION

The aforementioned photographs were taken in April 2010 from plants growing in a greenhouse trial in Gilroy, Calif. USA. These plants were growing in 4 inch pots and were approximately 15-16 weeks of age.

The plant descriptions and measurements were taken in late May 2010 in Enkhuizen, Netherlands on about 12 week old plants that had been planted into 12 cm pots and were grown on benches in a greenhouse at a minimum temperature (heating temperature) of 12° C. From April on, a minimum night temperature of 8° C. was held, while day temperatures were much higher, depending on outdoor temperature.

Color references are made to The Royal Horticultural Society Colour Chart (R.H.S.) 2001.

TABLE 1

DIFFERENCES BETWEEN THE NEW VARIETY 'PUWYDENA' AND A SIMILAR VARIETY

| | 'Puwydena' | 'Sunmaref TP-V' (U.S. Plant Pat. No. 9,411) |
|---|---|---|
| Flower color: | Violet with white eye | Purple blue without eye |
| Earliness to flower: | Early | Late |
| Flower size: | Medium | Small |

Plant:
*Form, growth and habit*.—Herbaceous, initially spreading, later becoming decumbent to trailing.
*Plant height*.—About 8 cm.
*Plant height* (*inflorescence included*).—10-13 cm.
*Plant width*.—About 36 cm.
Roots:
*Number of days to initiate and produce roots*.—About 10-14 days at about 22 degrees C.
*Type*.—Fine, fibrous, free branching.
*Color*.—RHS N155B.
Foliage:
*Arrangement*.—Alternate, simple.
*Immature, leaf color, upper surface*.—RHS 137D.
*Lower surface*.—RHS 138B.
*Mature, leaf color, upper surface*.—RHS 137B.
*Lower surface*.—RHS138C.
*Length*.—3.8-5.4 cm.
*Width*.—2.2-3.4 cm.
*Shape*.—Ovate.
*Base shape*.—Acute to attenuate.
*Apex shape*.—Obtuse.
*Margin*.—Pinnatifid; entire but with incisions of about 0.9-1.2 cm.
*Texture, upper surface*.—Sparse short hairs.
*Lower surface*.—Short, stiff hairs mainly along with veins; some glandular hairs.
*Color of veins, upper surface*.—RHS 144A becoming indistinct.
*Color of veins, lower surface*.—RHS 145B.
*Petiole color*.—RHS 145B.
*Length*.—0.1-0.4 cm.
*Diameter*.—0.1-0.2 cm.
*Texture*.—Hirtellous.
Stem:
*Characteristics*.—Side branches develop potentially at every node.
*Color of stem*.—RHS 137C.
*Length of stem*.—Approximately 16-28 cm.
*Diameter*.—0.3 cm.
*Length of internodes*.—Approximately 5-6 cm.
*Texture*.—Densely hirsute.
*Color of peduncle*.—RHA 138A.
*Length of peduncle*.—5-8 cm.
*Peduncle diameter*.—0.15-0.2 cm.
*Texture*.—Densely covered with short glandular hairs, hirtellous.
Inflorescence:
*Type*.—Umbel-like, but actually a spike, umbrella-shaped to roughly semi-spherical.
*Blooming habit*.—Flowers continuously.
*Quantity of inflorescences per plant*.—15-20.
*Lastingness of individual blooms on the plant*.—About 6 days in the greenhouse.
*Fragrance*.—None.
*Inflorescence horizontal diameter*.—3.8-5.0 cm.
*Inflorescence depth* (*height*).—2.0-3.2 cm.
*Quantity of flowers and buds per inflorescence*.—20-30.
Bud (just when starting to show color):
*Color*.—RHS N155B.
*Length*.—2.1-2.5 cm.
*Width*.—0.5-0.7 cm.
*Shape*.—Mainly tube-shaped with a bulbous end.
Floret:
*Form and type*.—Sessile; salverform, composed of 5 partly fused petals with a base of a narrow tube.
*Immature color, upper surface*.—RHS 83B with an eye color of RHS 155B of about 0.3 cm wide. Lower surface: RHS 83C.
*Mature color, upper surface*.—RHS 83B with an eye color of about RHS 155B of about 0.3 cm wide. Lower surface: RHS 83D.
*Floret diameter*.—1.8-2.2 cm.
*Floret depth*.—1.8-2.3 cm.
*Length of petals*.—0.6-0.9 cm.
*Width of petals*.—0.6-1.0 cm.
*Petal shape*.—Obcordate.
*Apex shape*.—Emarginate.
*Margin*.—Entire.
*Petal texture, upper surface*.—Smooth and glabrous. Lower surface: Smooth and glabrous.
*Corolla tube length*.—1.7-2.0 cm.
*Corolla tube color inside*.—RHS 150C. Tube color outside: RHS 150D.
*Corolla texture, inside*.—Glabrous. Outside: Glabrous basally; glandular hairs at the flare.
Calyx:
*Type*.—Five sepals whose margins are fused to each other along their length, with a transparent membrane of less than 0.1 cm in width and with one smaller sepal attached to the base of the calyx.
*Color of sepals*.—RHS 143B to RHS 143C.
*Length of sepals*.—1.0-1.2 cm.
*Width of sepals*.—0.2-0.3 cm.
*Sepal shape*.—Linear.
*Apex shape*.—Acute.
*Margins*.—Entire.
*Texture*.—Densely covered with short hair.
Reproductive organs:
*Pistil*.—1.
*Length*.—1.4-2.0 cm.
*Style color*.—RHS 144B.
*Style length*.—1.3-1.8 cm.
*Stigma color*.—RHS 143B.
*Stamens*.—Anthers and filaments fused to upper half of corolla tube; four anthers with two pollen sacs per anther.
*Color of filaments*.—RHS 150D to RHD 155B.
*Length filaments*.—0.1 cm.
*Anther color*.—RHS N144B.
*Length of anthers*.—0.1-0.15 cm.
*Color of pollen*.—RHS 1B.
*Pollen amount*.—Moderate.
*Fertility/seed set*.—Has not been observed on this hybrid.
Disease/pest resistance: Disease/pest resistance has not been observed on this hybrid.

What is claimed:

1. A new and distinct variety of *Verbena* plant named 'Puwydena' substantially as illustrated and described herein.

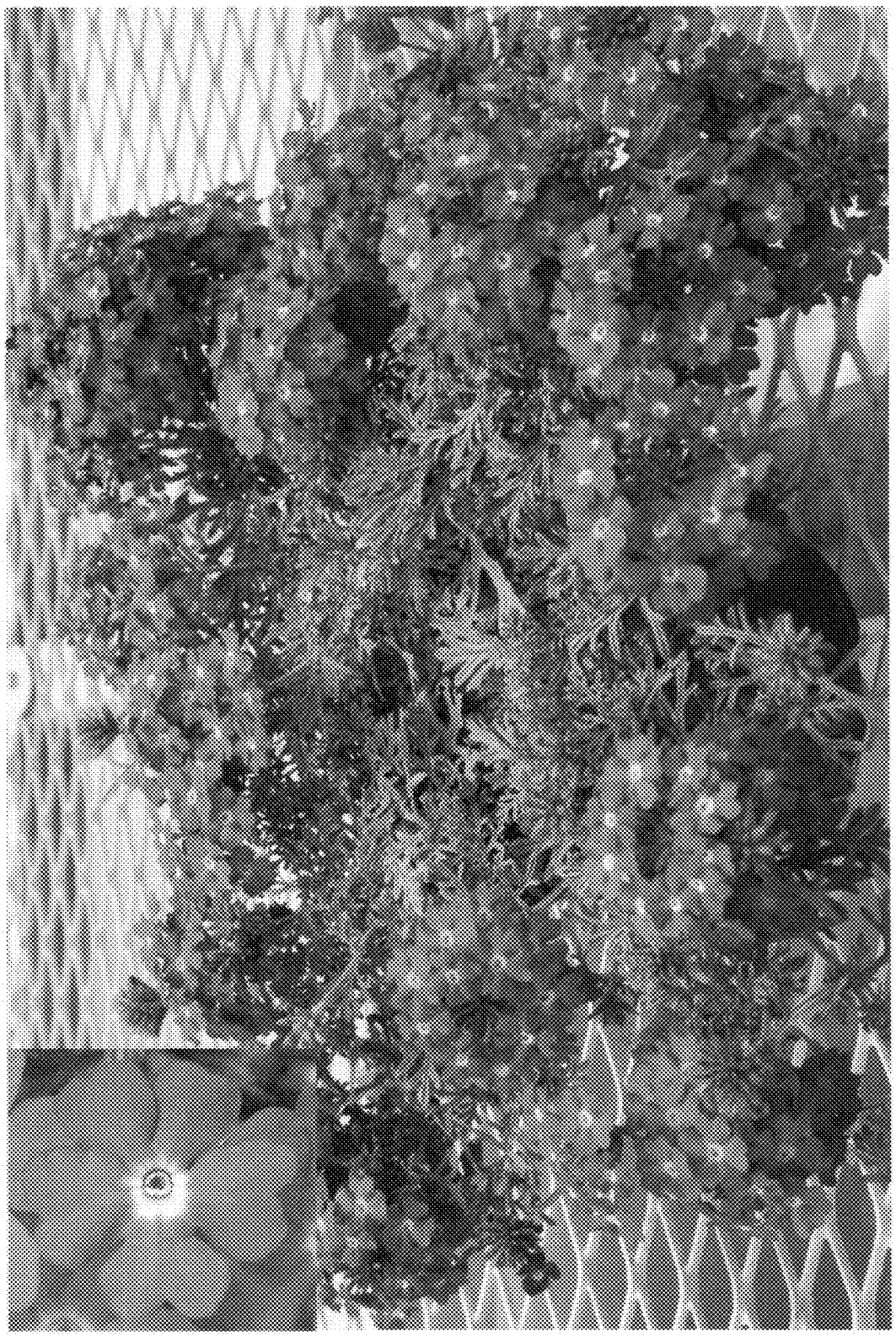

* * * * *